United States Patent [19]

Louderback et al.

[11] 4,279,775

[45] Jul. 21, 1981

[54] BLOOD GAS CONTROL

[76] Inventors: Allan L. Louderback, 9661 Longden Ave., Temple City, Calif. 91780; Paul R. Szatkowski, 24 Winthrop Rd., Bethel, Conn. 06801

[21] Appl. No.: 108,480

[22] Filed: Dec. 31, 1979

[51] Int. Cl.³ ............................................. G01N 33/48
[52] U.S. Cl. .................................. 252/408; 23/230 B; 23/928
[58] Field of Search .............. 252/408; 23/230 B, 928; 356/39

[56] References Cited

U.S. PATENT DOCUMENTS

| 3,859,049 | 1/1975 | Ware et al. | 252/408 |
|---|---|---|---|
| 3,876,375 | 4/1975 | Maurukas | 252/408 |
| 3,973,913 | 8/1976 | Louderback | 252/408 |
| 4,001,142 | 1/1977 | Turner | 252/408 |
| 4,056,484 | 11/1977 | Heimburger et al. | 252/408 |
| 4,116,336 | 9/1978 | Sorensen et al. | 252/408 |
| 4,121,905 | 10/1978 | Maurukas | 252/408 |
| 4,126,575 | 11/1978 | Louderback | 252/408 |
| 4,141,856 | 2/1979 | Dorwart, Jr. et al. | 252/408 |
| 4,151,108 | 4/1979 | Sorensen et al. | 252/408 |
| 4,163,734 | 8/1979 | Sorensen et al. | 252/408 |
| 4,189,401 | 2/1980 | Louderback | 252/408 |
| 4,199,471 | 4/1980 | Louderback et al. | 252/408 |

Primary Examiner—Teddy S. Gron

[57] ABSTRACT

There is disclosed a synthetic liquid control standard for use in the quality assurance of blood gas instrumentation systems which comprises an aqueous solution of a dye buffered to a pH of from about 7.1 to about 7.7 and containing sufficient bicarbonate ion to provide a $pCO_2$ of from about 20 to about 80, ethylene glycol to provide a viscosity of from about 3 to about 9 centipoises and gaseous oxygen to provide a $pO_2$ of from about 50 to about 400 retained in a sealed receptacle.

11 Claims, No Drawings

BLOOD GAS CONTROL

BACKGROUND OF THE INVENTION

This invention relates to a synthetic liquid control standard for use in the quality assurance of blood gas instrumentation systems.

The determination of blood pH, $pCO_2$ and $pO_2$ is an established diagnostic procedure which is used in conjunction with certain medical and surgical treatments. It is important to know the condition of the patient's circulating blood in terms of its acid-base balance, electrolytes and blood gas levels at all times during such procedures.

Various instrumentation systems have been developed for the determination of the parameters which comprise the blood gases and acid-base balance. These instrumentation systems generally are capable of measuring blood pH, $pCO_2$ and $pO_2$. Illustrative of such instrumentation systems are those described in U.S. Pat. Nos. 3,658,478; 3,652,843; 3,763,422; 3,654,445; and 3,874,850. Commercially available instrumentation systems are the Corning 175 Automatic pH/Blood Gas System; the ABL1 Acid-Base Laboratory of the London Company, Radiometer Copenhagen; the IL 113 pH/Blood Gas Analyzer from Instrumentation Laboratory; and the Technicon BGII pH/Blood Gas System.

It is common practice to employ control solutions for verifying the accuracy and reliability of these instrumentation systems. Illustrative of these control solutions for use in blood gas determination systems are the blood gas control standards described in U.S. Pat. Nos. 3,973,913 and 4,126,575. These compositions contain stabilized red blood cells in a buffered solution of bicarbonate ions with an appropriate gaseous head space packaged in a sealed receptacle.

Another typical blood gas control is disclosed in U.S. Pat. No. 4,001,142. This control standard comprises an aqueous solution of a dye, buffering agent, a lower alkyl acid such as acetic acid, triethanolamine, bicarbonate ions and dissolved gases. A variation of this type of blood gas control, described in German Offenlegungsshrift No. 2,727,140 and U.S. Pat. No. 4,163,734, comprises an aqueous solution which contains buffer and a dye (Ponceau 4R) emulsified with perfluorotributlyamine and has dissolved gases in equilibrium therewith.

The blood gas instrumentation systems of the current state of the art generally employ electrodes for measuring pH, $pCO_2$ and $pO_2$. For example, the hydrogen ion concentration may be monitored with a pH responsive glass electrode in cooperation with a Ag/AgCl reference electrode; the partial pressure of carbon dioxide ($pCO_2$) may be sensed in the circulating fluid with a $pCO_2$ electrode and the partial pressure of oxygen ($pO_2$) may be similarly monitored with an oxygen-sensing electrode. These gas sensing electrodes will be adapted with a selectively permeable membrane over the tip to permit passage of the relevant gas to be sensed. These membranes may be comprised of materials such as silicone rubber, Teflon ® plastic and the like semi-permeable materials which are permeable to gas but impermeable to liquid.

In actual practice over a period of time, there is a tendency of protein material from the blood samples applied to the blood gas measuring instrument to accumulate on the electrode membrane and thereby plug up the pores of the semi-permeable membrane material or otherwise contaminate the instrument tubing. The present inventors have now developed a completely synthetic liquid control standard for use in blood gas instrumentation systems which provides adequate blood gas control and at the same time promotes the clearing off of protein material from the electrode membrane and tubing system.

DESCRIPTION OF THE INVENTION

In brief, the disclosed synthetic blood gas control standard comprises an aqueous solution of a dye buffered to a pH of from about 7.1 to about 7.7 and containing sufficient bicarbonate ion to provide a $pCO_2$ of from about 20 to about 80, ethylene glycol to provide a viscosity of from about 3 to about 9 centipoises and gaseous oxygen to provide a $pO_2$ of from about 50 to about 400 retained in a sealed receptacle.

The blood gas control of this invention thereby provides a synthetic composition that does not contain natural biological material such as blood cells or proteinaceous blood serum or plasma components. Nevertheless, it has a viscosity approaching that of, or similar to that of blood and can, therefore, flow through the instrumentation system tubing in a manner resembling normal blood rather than water or the usual aqueous synthetic blood gas control solutions. Since the blood gas measuring instruments are adapted with a vacuum system to draw in blood samples for the appropriate blood gas analyses, the liquid control standard of this invention which has a viscosity approaching that of, or similar to that of blood will flow through the instrument tubing system substantially similar to that of blood. It will thereby provide a better control standard and provide more accurate representation of normal blood than a less viscous liquid control standard.

Viscosity is usually expressed in dyne-seconds per square centimeter or poises. One poise equals 100 centipoises. The absolute viscosity of water at 20° C. for calibration purposes is 0.01002 poises as reported by Swindells et al, *Journal of Research, National Bureau of Standards*, 48, 1 (1952). Blood has a viscosity about 5 to 6 times greater than water, or about 5 to 6 centipoises.

Ethylene glycol has a viscosity at 20° C. of 19.9 centipoises. Incorporation of from about 15 to about 45 volume percent of ethylene glycol in the aqueous solution thus provides the desired viscosity of from about 3 to about 9 centipoises to the solution. The presence of said amount of ethylene glycol in the aqueous solution also enables the control solution to promote the clearing of protein material from the surface of the electrode membranes and the instrument tubing system as the control standard solution is applied to the instrument. That is, the ethylene glycol reduces the surface tension or the tendency of protein contaminants to cling to the surface of the membrane or tubing materials. This surface tension reduction property of the ethylene glycol also aids in the removal of the entire liquid control standard contents from the receptacle in which it is contained, especially that portion of the solution that tends to cling to the top of a breakaway glass ampule In practice, the ampule containing the control standard sample is shaken prior to use to provide improved equilibrium of the liquid and dissolved gases. This procedure tends to cause some of the sample to cling to the upper portion of the ampule. As the top of the ampule is removed, the remainder of the solution in the ampule will be less than its stated amount and could cause inaccuracy in its measurement as applied to the instrument.

The control standard of this invention contains an appropriate dye to indicate to the user the relative acid-base balance or blood gas metabolic condition to be represented by the control standard, for example, normal, acidosis, alkalosis or hyper-oxygenated blood conditions. As an example, a normal blood gas control standard with a pH of about 7.4, $pCO_2$ about 40 and $pO_2$ about 100 can be indicated by a yellow dye solution. Preferably, about 100 mg FD & C Yellow No. 5 (tartrazine) is used in about 500 ml of aqueous solution for the normal blood control standard. The acidosis metabolic condition with a pH of about 7.2, $pCO_2$ about 20 and $pO_2$ about 150 can be indicated by a red dye solution. Preferably, about 100 mg FD & C Red No. 40 (C.I. 16035) is used in about 500 ml of aqueous solution for the acidosis blood control standard. The alkalosis metabolic condition with a pH of about 7.6, $pCO_2$ about 60 and $pO_2$ about 60 can be indicated by a blue dye solution. Preferably, about 100 mg Peacock Blue is used in about 500 ml of aqueous solution for the alkalosis blood control standard. The hyper-oxygenated blood gas condition with normal pH of about 7.4 and $pCO_2$ about 60 but having elevated $pO_2$ of about 400 can be indicated by a green dye solution. The green dye solution is preferably made by combining about 50 mg FD & C Yellow No. 5 with about 50 mg Peacock Blue in about 500 ml of aqueous solution. Other such representative dye solutions to provide appropriate color distinctions for the various blood gas conditions encountered in patients will be apparent to the person skilled in the art and it will be understood that the invention is not limited to the aforesaid illustrative examples of dyes and dye solutions.

In order to provide the desired pH for the respective normal, acidosis or alkalosis conditions, a buffer material should be selected which had a $pK_a$ close to the desired working pH. A particularly useful buffer material for providing the desired pH conditions in the control solution of this invention is N-2-hydroxyethylpiperazine-N'-2-ethanesulfonic acid (HEPES) which has a $pK_a$ of 7.55 at 20° C. Other suitable buffer materials are, for example, N-tris(hydroxymethyl)methyl-2-aminoethanesulfonic acid (TES), which has a $pK_a$ of 7.50 at 20° C.; N,N-bis(2-hydroxyethyl)-2-aminoethanesulfonic acid (BES) which has a $pK_a$ of 7.15 at 20° C.; 3-(N-morpholino)propanesulfonic acis (MOPS), which has a $pK_a$ of 7.20 at 20° C.; and Piperazine-N-N'-bis(2-ethanesulfonic acid) (PIPES), which has a $pK_a$ of 6.8 at 20° C. These and other such suitable buffer materials, including the sodium salt derivatives, are described by Good et al, Biochemistry 5, 467–77 (1966)

The desired $pCO_2$ level is provided in part by addition of bicarbonate ion, for example, $NaHCO_3$, to the aqueous solution until a $pCO_2$ of from about 20 to about 80 is reached. The desired $pO_2$ level of from about 50 to about 400 is facilitated by addition of gaseous oxygen to the solution or the head space in the receptacle containing the aqueous solution. Addition of gaseous carbon dioxide similarly can facilitate maintenance of the aforesaid desired $pCO_2$ levels.

The final control standard solution is retained in a sealed or air-tight receptacle such as, for example, a glass vial or ampule to retain the desired gas equilibrium. The head space in the receptacle can be filled with an appropriate gas to facilitate the provision of the aforesaid $pCO_2$ and $pO_2$ conditions. For example, for the acidosis blood gas control, normal room air (about 21% oxygen and 78% nitrogen) preferably is used. For the normal blood gas control a mixture of about 5% carbon dioxide, 12% oxygen and 83% nitrogen preferably is used. For the alkalosis blood gas control a mixture of about 7% carbon dioxide, 7% oxygen and 86% nitrogen preferably is used. For the hyper-oxygenated blood gas control a mixture of about 40–60% oxygen and 40–60% nitrogen preferably is used. It will be appreciated that any other inert gas can be used as a substitute for part or all of the nitrogen portion of the head space in the foregoing illustrative examples.

The following specific and detailed example will further illustrate the invention although it will be appreciated that this example is not meant to restrict the invention to the specific details found in such example.

EXAMPLE

A buffer solution is prepared to comprise a 150 millimolar solution of HEPES by dissolving 35.745 grams of HEPES in 800 ml deionized water. Sufficient 4 N NaOH is added to adjust the pH to 7.400. Ethylene glycol is then added in an amount of 200 ml to bring the total volume to 1000 ml and provide a buffer/glycol solution containing 150 mM HEPES buffer at pH 7.400 (at room temperature of about 22°–25° C.) in a 20% ethylene glycol solution. An additional liter of the buffer/glycol solution is made in the same manner to provide two liters for this example.

Four separate aqueous dye/buffer/glycol solutions are then made up by dissolving three basic dyes in buffer/glycol solutions as prepared above in proportions as follows:

Acidosis—red solution—100 mg of FD & C Red No. 40 in 500 ml of the buffer/glycol solution.

Normal—yellow solution—100 mg of FD & C Yellow No. 5 in 500 ml of the buffer/glycol solution.

Alkalosis—blue solution—100 mg of Peacock Blue in 500 ml of the buffer/glycol solution.

Hyper-oxygenated—green solution—50 mg of Peacock Blue and 50 mg of FD & C Yellow No. 5 in 500 ml of the buffer/glycol solution.

Since the blood gas instrumentation systems of the current state of the art generally measure at 37° C. rather than at normal room temperature, the pH of the aforesaid dye/buffer/glycol solutions are adjusted to the desired levels (acidosis—pH 7.2; normal—pH 7.4; alkalosis—pH 7.6; and hyper-oxygenated—pH 7.4) by addition of 1 N HCl or 1 N NaOH as required to agree with the instrument pH at 37° C.

A solution of 1 M $NaHCO_3$ is then added to the dye/buffer/glycol solutions in small increments until the desired $pCO_2$ levels are reached as follows:

| Acidosis | $pCO_2$ 20 |
| Normal | $pCO_2$ 40 |
| Alkalosis | $pCO_2$ 60 |
| Hyper-oxygenated | $pCO_2$ 40 |

The above prepared solutions are then filled into glass ampules of the top break-away type (capacity of 5 ml each). Each ampule is filled to a level of 2 ml. The head space in the ampule is then flushed with the desired gaseous mixtures as follows:

Acidosis—normal room air of about 21% oxygen and 78% nitrogen

Normal—5% carbon dioxide, 12% oxygen and 83% nitrogen

Alkalosis—7% carbon dioxide, 7% oxygen and 86% nitrogen

Hyper-oxygenated 60% oxygen and 40% nitrogen

The ampules are then flame sealed to provide an air-tight closure and the packaged product is stored at normal room temperature (about 22°–25° C.). The final product has a viscosity of about 5 to 6 centipoises and when applied to blood gas instruments flows in a manner resembling normal blood in viscosity and prevents the accumulation and contamination of the instrument membranes and tubing systems with protein from the blood samples applied to the instrument. The final product can be continuously stored at normal room temperatures and it is not necessary to store at refrigerated temperatures such as at 2° to 8° C. as required by the biological compositions of U.S. Pat. Nos. 3,876,375 and 4,121,905. The glycol in the control standard of this invention also acts as a stabilizer and preservative and, thus, enables one to avoid the autoclaving that is otherwise required for sterility as seen from U.S. Pat. No. 4,001,142.

Substantially similar results as obtained in the above EXAMPLE are obtained when the dye/buffer/glycol solutions are adjusted to the following pH levels:

| acidosis | pH 7.1 to 7.3 |
| normal | pH 7.31 to 7.5 |
| alkalosis | pH 7.51 to 7.7 |
| hyper-oxygenated | pH 7.31 to 7.5 |

In the above EXAMPLE the final $pO_2$ levels are as follows:

| acidosis | $pO_2$ 150 |
| normal | $pO_2$ 100 |
| alkalosis | $pO_2$ 60 |
| hyper-oxygenated | $pO_2$ 400 |

Other suitable adjustments in $pO_2$ and $pCO_2$ can be made as desired within the disclosed ranges. For example, in the hyperoxygenated blood gas control, the $pO_2$ can be adjusted to other levels within a preferred range of 200 to 400, and the $pCO_2$ can be adjusted to other levels within a preferred range of 20 to 60 with substantially similar results as obtained in the above EXAMPLE.

Still other examples will be apparent to the person skilled in the art after reading the present disclosure without departing from the spirit and scope of the invention and it is intended that all such examples shall be included witin the scope of the appended claims.

What is claimed is:

1. A completely synthetic liquid control standard for use in the quality assurance of blood gas instrumentation systems comprising an aqueous solution of a dye buffered to a pH of from about 7.1 to about 7.7 and containing sufficient bicarbonate ion to provide a $pCO_2$ of from about 20 to about 80, ethylene glycol to provide a viscosity of from about 3 to about 9 centipoises and promote clearing of proteinaceous material from said instrumentation systems and gaseous oxygen to provide a $pO_2$ of from about 50 to about 400 retained in a sealed receptacle.

2. The control standard of claim 1 in which the aqueous solution is buffered with N-2-hydroxyethylpiperazine-N'-2-ethanesulfonic acid buffering agent.

3. The control standard of claim 1 in which the ethylene glycol provides a viscosity of about 5 to 6 centipoises.

4. The control standard of claim 1 in which the dye is selected from the group consisting of FD & C Red No. 40, FD & C Yellow No. 5, Peacock Blue and mixtures of said FD & C Yellow No. 5 and Peacock Blue.

5. The control standard of claim 1 in which the aqueous solution is buffered with N-2-hydroxyethylpiperazine-N'-2-ethanesulfonic acid, the ethylene glycol provides a viscosity of about 5 to 6 centipoises, the dye is FD & C Red No. 40, the pH is about 7.2, the $pCO_2$ is about 20 and the $pO_2$ is about 150.

6. The control standard of claim 1 in which the aqueous solution is buffered with N-2-hydroxyethylpiperazine-N'-2-ethanesulfonic acid, the ethylene glycol provides a viscosity of about 5 to 6 centipoises, the dye is FD & C Yellow No. 5, the pH is about 7.4, the $pCO_2$ is about 40 and the $pO_2$ is about 100.

7. The control standard of claim 1 in which the aqueous solution is buffered with N-2-hydroxyethylpiperazine-N'-2-ethanesulfonic acid, the ethylene glycol provides a viscosity of about 5 to 6 centipoises, the dye is Peacock Blue, the pH is about 7.6, the $pCO_2$ is about 60 and the $pO_2$ is about 60.

8. The control standard of claim 1 in which the aqueous solution is buffered with N-2-hydroxyethylpiperazine-N'-2-ethanesulfonic acid, the ethylene glycol provides a viscosity of about 5 to 6 centipoises, the dye is a mixture of FD & C Yellow No. 5 and Peacock Blue, the pH is about 7.4, the $pCO_2$ is about 40 and the $pO_2$ is about 400.

9. The method of making a synthetic liquid control standard for use in the quality assurance of blood gas instrumentation systems and having a viscosity resembling that of blood comprising admixing an aqueous solution of a dye buffered to a pH of from about 7.1 to about 7.7 with sufficient bicarbonate ion to provide a $pCO_2$ of from about 20 to about 80, ethylene glycol to provide a viscosity of from about 3 to about 9 centipoises and gaseous oxygen to provide a $pO_2$ of from about 50 to about 400 retained in a sealed receptacle.

10. The control standard of claim 1 in which the receptacle contains a head space filled with a gaseous mixture comprising oxygen and nitrogen.

11. The control standard of claim 10 in which the gaseous mixture includes carbon dioxide.

* * * * *